US005425859A

United States Patent [19]
Tench et al.

[11] Patent Number: 5,425,859
[45] Date of Patent: Jun. 20, 1995

[54] METHOD AND APPARATUS FOR ASSESSING AND RESTORING SOLDERABILITY

[75] Inventors: D. Morgan Tench, Ventura; Dennis P. Anderson, Newbury, both of Calif.

[73] Assignee: Rockwell International Corporation, Seal Beach, Calif.

[21] Appl. No.: 60,328

[22] Filed: May 11, 1993

Related U.S. Application Data

[63] Continuation-in-part of Ser. No. 706,142, May 28, 1991, Pat. No. 5,262,022.

[51] Int. Cl.⁶ .............................................. G01N 27/26
[52] U.S. Cl. .................................... 204/153.1; 204/400; 204/412; 204/434
[58] Field of Search .............. 204/153.1, 153.11, 400, 204/404, 412, 434

[56] References Cited

U.S. PATENT DOCUMENTS

| | | | |
|---|---|---|---|
| 2,390,591 | 12/1945 | Janes | 204/294 |
| 3,032,493 | 5/1962 | Coulson et al. | 204/405 |
| 3,102,085 | 8/1963 | Edwards et al. | 204/290 F |
| 3,309,233 | 3/1967 | McPheeters et al. | 204/422 |
| 3,421,989 | 1/1969 | Haagen-Smit | 204/413 |
| 3,684,679 | 8/1972 | Smith et al. | 204/404 |
| 3,838,021 | 9/1974 | Arbiter | 204/422 |
| 3,943,043 | 3/1976 | Billington et al. | 204/434 |
| 4,132,605 | 1/1979 | Tench et al. | 204/434 |
| 4,427,496 | 1/1984 | Katz | 204/153.1 |
| 4,654,126 | 3/1987 | Amelio | 204/434 |
| 4,718,990 | 1/1988 | Hashimoto et al. | 204/434 |
| 4,725,339 | 2/1988 | Bindra et al. | 204/434 |
| 5,104,494 | 4/1992 | Tench et al. | 205/125 |

OTHER PUBLICATIONS

Kolthoff et al, *Polarography*, 2d. ed., vol. 1, (1952), p. 395.

Tench et al., "Electrochemical Assessment of Sn-Pb Solderability," Plating and Surface Finishing, pp. 44–46, Aug. 1990.

*Primary Examiner*—T. Tung
*Attorney, Agent, or Firm*—John C. McFarren

[57] ABSTRACT

A sequential electrochemical reduction method and apparatus are provided for assessing and restoring solderability of electronic component leads. The method detects and quantifies the presence of metallic oxides that are detrimental to solderability by sequential electrochemical reduction in contact with an electrolyte in an inert atmosphere. A cathode having a high hydrogen overvoltage is placed in contact with the electrolyte. A solderable portion of the component to be tested is placed in contact with the cathode and the electrolyte. An inert counter electrode and a reference electrode are also placed in contact with the electrolyte. A current is passed between the cathode and inert electrode, and the voltage and current are measured as a function of time during reduction of metallic oxides on the solderable portions of the component. The measurements of voltage, current, time, and charge density may be compared with baseline data from specimens having known oxide compositions that correlate with degradation of solderability.

13 Claims, 4 Drawing Sheets

METHOD AND APPARATUS FOR ASSESSING AND RESTORING SOLDERABILITY

RELATED APPLICATION

This application is a continuation-in-part of U.S. patent application Ser. No. 706,142 filed May 28, 1991, which issued on Nov. 16, 1993, as U.S. Pat. No. 5,262,022.

TECHNICAL FIELD

The present invention relates to chronopotentiometric methods of analysis and, in particular, to a sequential electrochemical reduction method and apparatus for assessing and restoring the solderability of electronic component leads and printed wiring boards.

BACKGROUND OF THE INVENTION

A major cost problem experienced by the electronics industry is the loss of solderability of electronic components and printed circuit boards, particularly during storage. Poor solderability of component leads and printed wiring boards is believed to account for as much as 75% of solder joint failures. Because humid environments are known to exacerbate the problem, an electrochemical mechanism is clearly the cause of solderability degradation. In the lead-tin-copper solder system, for example, previous studies have determined that oxidation of the tin-lead (Sn—Pb) surface and underlying copper-tin (Cu—Sn) intermetallic layers is involved in the degradation process. In the past, however, the nature of the various oxides and their roles in the degradation of solderability remained obscure.

Traditional techniques typically employed in the prior art for surface analysis of circuit boards provide only subjective indicators of solderability. Presently used production test methods are also destructive by nature. Because degradation of solderability is known to involve an electrochemical mechanism, it is believed that solderability can be assessed more accurately and efficiently using electrochemical methods and apparatus that provide in situ quantitative analysis of metallic oxides known to degrade solderability. In particular, there is a need for quantitative, nondestructive, electrochemical methods of analyzing and/or restoring solderability that are easily applied for testing off-the-shelf components, such as printed wiring boards and dual-in-line package (DIP) components, for example, for process control in the production environment, and for restoring solderability of degraded components.

SUMMARY OF THE INVENTION

The present invention comprises a method of sequential electrochemical reduction analysis "SERA"), including apparatus for assessing and/or restoring (i.e., improving) solderability of electronic component leads and printed wiring boards. The SERA method detects and quantifies metallic oxides known to degrade solderability when present on metal surfaces that are to be soldered. The method of the present invention is applicable to the lead-tin-copper solder system, as well as to solder systems comprising other metals and alloys. The invention comprises a nondestructive method that provides a quantitative measure of the solderability of electronic components and printed wiring boards. Furthermore, the method may be used to restore and ensure the solderability of electronic components and printed wiring boards.

The SERA method of the present invention is performed by placing the solderable portion of the component or circuit board to be tested in contact with an electrolyte, such as a borate buffer solution. The portion of the component in contact with the electrolyte forms a first electrode. A second, inert electrode and a third, reference electrode, such as a saturated calomel electrode, are also placed in the electrolyte. A small cathodic current is passed from the inert electrode to the tested component, and the potential between the component and the reference electrode is recorded as a function of time. Alternatively, current can be recorded as a function of time under conditions of known electrical potential (i.e., measured, metered, ramped, or otherwise controlled). In systems where the second, inert electrode has a stable voltage at the low currents used, it can also function as the reference electrode, thereby eliminating the need for a separate reference electrode. In a plot of the electrode potential versus time (or charge passed—i.e., current multiplied by time), a series of inflection points or plateaus are observed in which the voltage level identifies a particular oxide or oxide mixture, and the associated charge is a measure of the thickness of that particular oxide. Because the SERA process reduces metallic oxides back to their metallic state, the method actually restores solderability of the treated part to the optimum level.

The results achieved from the sequential electrochemical reduction performed on the tested component are compared to similar analytical results from baseline experiments on specimens exposed to various aging treatments. As determined by the wetting balance method, solderability of aged specimens has been found to correlate with the results of sequential electrochemical reduction analysis (SERA). Therefore, the analytical results from the tested component can be compared with baseline results obtained from aged specimens having known oxide and solderability characteristics to determine the solderability of the tested component. Wetting balance measurements have also shown that the solderability of degraded components is restored by the SERA treatment.

A principal object of the present invention is to analyze and improve the solderability of electronic components and circuit boards. A feature of the invention is a method of sequential electrochemical reduction analysis (SERA) that can be applied to all types of electronic components to identify and eliminate the metallic oxides that cause loss of solderability. An advantage of the invention is a nondestructive, quantitative, and easily performed method of determining and restoring the solderability of electronic components. Information derived from the method is useful for controlling production soldering processes and improving manufacturing processes for printed wiring boards and other electronic components.

BRIEF DESCRIPTION OF THE DRAWINGS

For a more complete understanding of the present invention and for further advantages thereof, the following Detailed Description of the Preferred Embodiments makes reference to the accompanying Drawings, in which.

DETAILED DESCRIPTION OF THE PREFERRED EMBODIMENTS

Solder coatings are widely used to protect copper in printed wiring boards and electronic component leads from oxidation that can lead to loss of solderability. A typical solder coating comprises eutectic Sn—Pb, for example, that can be applied directly by hot dipping or can be electroplated and then densified by reflowing (melting). Solderability of a finished component is affected by the metal ratios of the deposited solder, the thickness of the coating, the type of solder bath, the plating conditions, the presence of organic contaminants from plating bath additives, and the generation of breakdown products. Even when sufficiently thick and properly applied, however, such coatings slowly lose solderability during normal storage. Oxidation and solderability loss of Sn—Pb coatings can be much faster as a result of insufficient coating thickness, poor coating quality, and/or a poor storage environment.

The present invention comprises improvements to both the method and apparatus for sequential electrochemical reduction analysis (SERA) of solderable portions of electronic components. The invention provides both nondestructive assessment of solderability loss associated with surface oxides on metals and actual restoration of solderability. The method can be applied to components of nearly any geometry, including printed wiring board surface pads and through-holes, dual-in-line package leads, grid arrays, solder bumps, and various other component leads. The method can also be used to detect the presence of metal sulfides in some cases. The type and amount of surface oxides detected on solder coatings has been shown to correlate with solderability, as determined by the well known wetting balance method. In addition, the primary cause of solderability degradation for relatively thick Sn and Sn—Pb coatings has been determined to be the presence of surface metallic oxides, particularly the higher tin oxides that include significant amounts of $SnO_2$.

BASELINE EXPERIMENTS

For initial tests, a typical specimen was a 1.5 mm diameter hard Cu wire, 2.5 cm in length, which was masked with Teflon ® heat-shrink tubing to expose a 1 cm long section with a rounded end. The exposed section was plated with 10 μm of Cu from a standard non-additive pyrophosphate bath at 55° C., then with 12 μm of eutectic Sn—Pb from a standard fluoroborate bath at room temperature. During plating the wire cathode was rotated at 2000 rpm to control mass transport in the solution. A 60/40 Sn—Pb ratio was verified by atomic absorption analysis of specimens dissolved in acid solution and by X-ray fluorescence analysis. The Sn—Pb coating was reflowed in water soluble oil at 235° C. for minimal time prior to use. For additional tests, specimens included printed wiring boards and 0.8 mm diameter Cu wire coated with Sn or Sn—Pb solder by dipping in molten solder after the surface had been treated with an RMA flux. Some specimens were subjected to anodization treatments at a constant current of 20 μA per $cm^2$ to produce samples having various oxide structures. The anodization was terminated when the anode voltage reached a particular value which was found to define the type and amount of oxide produced. The lower Sn oxides (predominantly SnO) are produced at voltages less than about 0.2 V versus the reference saturated calomel electrode (SCE). More positive voltages produced the higher Sn oxides, which contain significant amounts of $SnO_2$.

Electrochemical reduction of the oxides on the test specimens was performed at a constant reduction current of −20 μA per $cm^2$ in an argon-saturated pH 8.4 borate buffer solution (9.55 g/L sodium borate and 6.18 g/L boric acid) contained in a glass cell/reservoir using a platinum (Pt) counter electrode and a reference saturated calomel electrode (SCE). Other electrolytes compatible with the particular metal system under investigation (such as the Cu—Sn—Pb system, for example) may be used in conjunction with alternative types of reference electrodes and counter electrodes of other inert materials. To minimize electrolyte contamination by chloride, the SCE electrode was contained in a separate compartment (such as a glass tube, for example) electrically connected to the main compartment via a porous Vycor ® glass disk sealed to the end of the glass tube with heat-shrink Teflon ® tubing. For analysis of wire specimens, which contacted the electrolyte solution in the main cell compartment, the Pt electrode was also isolated via porous glass to avoid contamination of the solution by oxygen evolved anodically. For analysis of printed wiring board through-holes or surface pads, where the electrolyte solution was brought from a main reservoir to contact the surface to be analyzed, a Pt counter electrode was placed directly in the solution but at an adequate distance from the surface under analysis so that interference from oxygen reduction was avoided. All electrochemical experiments were performed using either a potentiostat-galvanostat (PAR model 173, EG&G Princeton Applied Research Corp., Princeton, N.J.) or a programmable current source (Keithley Instruments model 224 in conjunction with a Fluke model 8842 multimeter). Solderability tests were performed using either a modified Wilhelmy wetting balance in conjunction with a digital oscilloscope (Nicolet model 2090, Nicolet Instrument Corp., Madison, Wis.) or a Multicore universal solderability tester controlled by an IBM model XT personal computer.

During the reduction analysis, electrode potential versus the reference SCE electrode was recorded as a function of time. Inflection points, which are believed to correspond to the reduction of PbO, SnO, and SnO$_2$, were observed at approximately $-0.6$ V, $-0.9$ V, and $-1.1$ V, respectively. From cyclic voltametric measurements involving pure Pb and Sn electrodes, it was determined that there was a one-to-one correspondence between the anodic charge passed during formation of the oxides by anodization and the cathodic charge required for their reduction. This result indicates that the electrochemical reduction method of the present method provides a quantitative measure of the amount of each surface oxide present. In addition, the fact that such thick oxides can be sequentially reduced indicates appreciable oxide porosity. Highly oxidized specimens were consistently found to exhibit very poor solder wetting characteristics, thereby establishing a correlation between the presence of higher Sn oxides and the loss of solderability.

Figure 1A:
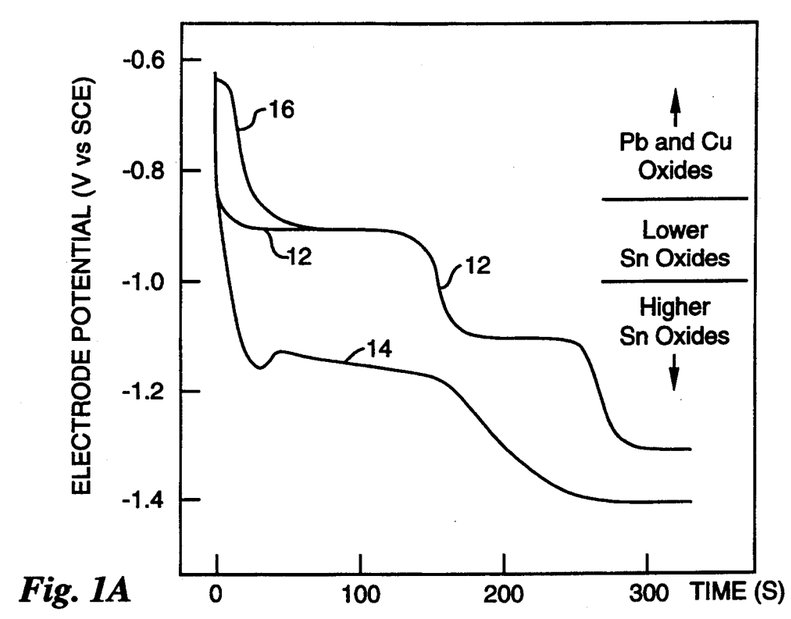
FIG. 1A is a graph of electrode potential versus time illustrating theoretical sequential electrochemical reduction analysis curves for solderable specimens having various metallic oxides.

FIG. 1A illustrates representative curves of the type obtained from sequential electrochemical reduction analysis of the oxides formed on Sn—Pb solder coatings on Cu substrates. These curves plot electrode potential versus time during reduction of the oxides. For the ideal case involving well-defined surface oxides that are all exposed to the electrolyte, shown by curve 12, the cathode voltage initially decreases to a plateau corresponding to reduction of the most easily reduced oxide. After the first oxide is completely reduced, the voltage decreases to the value required for reduction of the next most easily reduced oxide. This process is repeated until all oxides are reduced and a steady voltage corresponding to hydrogen evolution from water electrolysis is attained. Because the Sn oxides often occur as an intimate mixture, only one well-defined Sn voltage plateau with considerable wave tailing may be observed, as shown by curve 14. Therefore, it is convenient to refer to the Sn oxides as the lower oxides (believed to be predominantly SnO, which reduces at a voltage of approximately $-0.85$ V to $-1.0$ V versus the reference SCE electrode), and the higher oxides (believed to include significant amounts of SnO$_2$, which reduces at a voltage of approximately $-1.0$ V to $-1.4$ V). Negative voltage peaks, as shown on curve 14, are often observed and are believed to indicate a duplex structure having a blocking outer layer (of higher Sn oxides) that is more difficult to reduce than the underlying material.

By analysis of production printed wiring boards, the voltage of the mixed Sn oxide reduction plateau has been shown to correlate with the occurrence of soldering defects. As this voltage becomes more negative, the average number of soldering defects increases, showing that data from the sequential electrochemical reduction analysis (SERA) of the present invention can be used to predict solderability of printed wiring boards. These results also confirm laboratory studies which show that the primary cause of solderability loss of the Sn—Pb coating itself is the increase in the amount of SnO$_2$ in the surface oxide, which is reflected in the more negative reduction potential. Sequential electrochemical reduction analysis also detects oxidized Cu—Sn intermetallic layers, which produce a low voltage "shoulder" on the curve corresponding to reduction of the oxidized Cu species, as shown by curve 16 in FIG. 1A. Such Cu—Sn intermetallic oxidation, which severely degrades solderability, sometimes occurs at the rims of circuit board through-holes where the solder coating tends to be thin ("weak knees"). Because Pb oxides do not normally form in significant concentrations on Sn—Pb surfaces, the occurrence of a low-voltage shoulder (such as illustrated by curve 16 in FIG. 1A) is a reliable indicator of exposed Cu—Sn intermetallics.

Figure 1B:
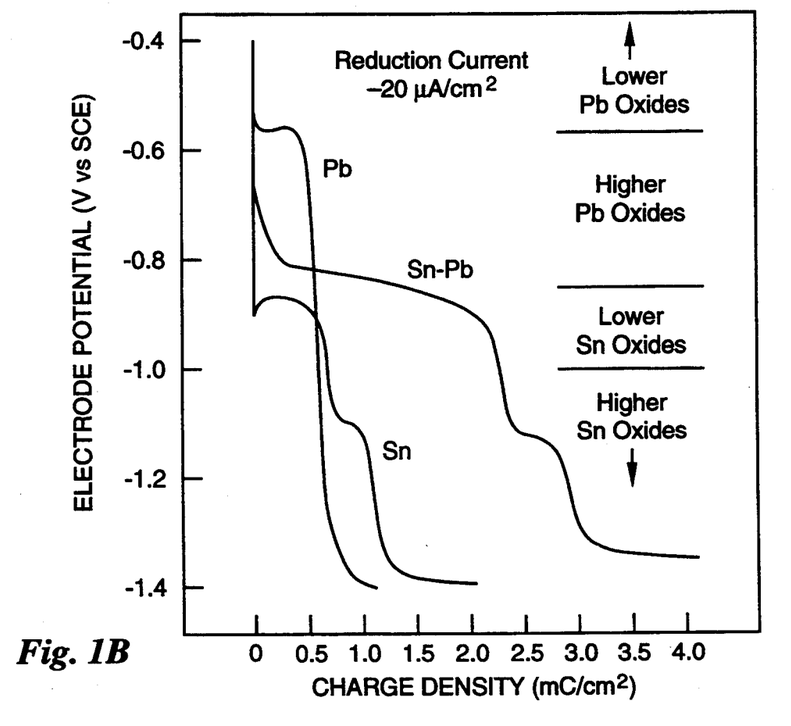
FIG. 1B is a graph of electrode potential versus charge density illustrating actual sequential electrochemical reduction analysis data for oxides of Sn, Pb, and eutectic Sn—Pb, and indicating the voltage ranges over which the various oxides are reduced.

FIG. 1b shows curves obtained from actual sequential electrochemical reduction analysis of the oxides formed on Sn, Pb, and eutectic Sn—Pb under mildly oxidizing conditions. These curves plot electrode potential (at a constant current of $-20$ $\mu$A per cm$^2$) versus charge density (which equals current density $\times$ time). The curves exhibit the well-defined plateaus typical of sequential reduction of individual oxide species.

Figure 2:
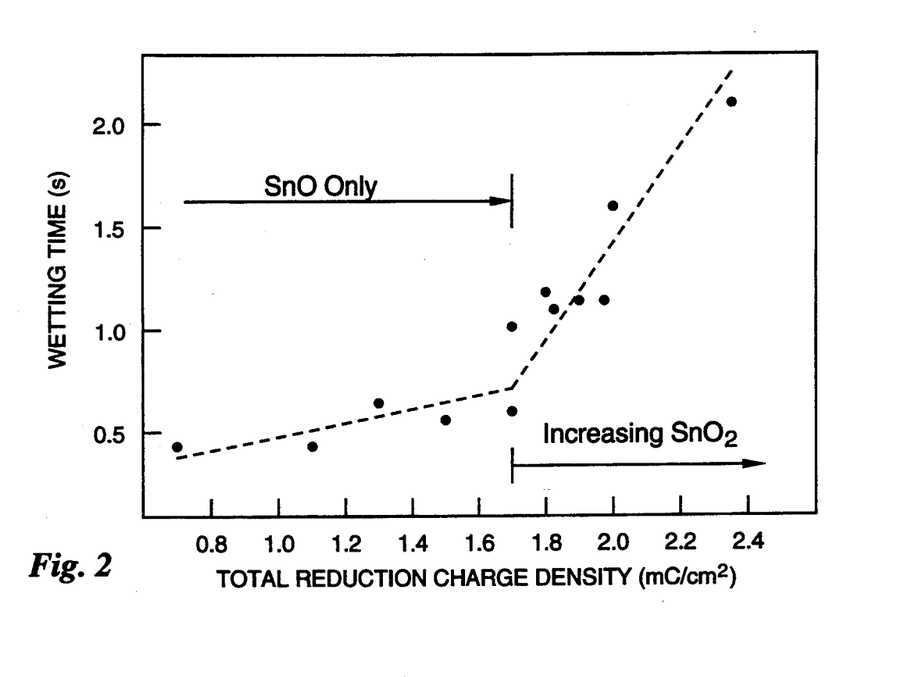
FIG. 2 is a plot of wetting times (from the wetting balance method) versus total reduction charge density (which corresponds to the amount and type of tin oxides present) that illustrates the detrimental effect (increased wetting time) of increasing amounts of Sn oxides, particularly $SnO_2$, on anodized Sn—Pb solder-coated copper wires.

FIG. 2 shows a correlation between the wetting time measured at 235° C. for anodized Sn-dipped Cu wire specimens and the amount and type of oxide indicated by SERA data for specimens prepared under identical conditions. For convenience, oxide amounts can be expressed in terms of the charge density required for reduction. The relationship between charge density and oxide thickness depends on the type of oxide (for SnO, 1 mC/cm$^2 \approx$ 1 nm oxide thickness, for example). For oxide amounts corresponding to total reduction charge densities up to about 1.6 mC/cm$^2$, for which SERA reduction voltages indicate the presence of only SnO, the effect on the wetting time is small. However, there is a significant increase in wetting time for oxides which comprise increasing amounts of SnO$_2$ (as indicated by a negative peak in the SERA curves). These results demonstrate that SERA data provide a reliable measure of solderability and that SnO$_2$ is the oxide most detrimental to solderability.

ASSESSING SOLDERABILITY

The present method of assessing and restoring solderability of an electronic component is essentially the same as described above in the baseline experiments. A solderable part of an electronic component to be tested (and restored), such as a metal lead, for example, is placed in contact with an electrolyte to form a first electrode. The electrolyte is chosen to facilitate reduction and minimize chemical dissolution of the metallic oxides of interest. A second, inert counter electrode (such as platinum or stainless steel, for example) is also placed in the electrolyte. A third, reference electrode, which may be placed in the electrolyte in a separate compartment isolated via porous glass, for example, may also be used. A constant cathodic current is passed between the component and the second electrode (to perform electrochemical reduction of the metallic oxides on the solderable parts of the component) while the potential between the component and the reference electrode is monitored as a function of time. In alternative embodiments, variable (or constant) current can be monitored as a function of time under conditions of constant (or variable) electrode potential. As described above, in systems where the second, inert electrode has a stable voltage at the low currents used, it can also function as the reference electrode, thereby eliminating the need for a separate reference electrode. When solderability restoration is the goal and it is not necessary to monitor the process, the current or voltage can be applied for a specified time without measuring the voltage and/or current response. The method of the present invention can be applied to various component configurations, including short and long component leads, solder bumps, and circuit board through-holes and surface mount pads. Solderability degradation associated with the oxides (and in some cases the sulfides) of Sn, Pb, Cu, Ag, Fe, and Ni can be determined using the sequential electrochemical reduction process of the present invention.

If the electrical lead used to establish contact to the part to be tested or restored also contacts the electrolyte solution, the contact lead should comprise a material having a high hydrogen overvoltage, such as lead, tin, mercury, indium, antimony, tantalum, bismuth, arsenic, carbon, cadmium, thallium, and alloys thereof, for example. If the contact material is copper, or other commonly used electrical conductor material, current can also pass through the contact wire to the electrolyte. This parasitic action causes measurement inaccuracy and/or restoration inefficiency resulting from breakdown of the electrolyte solution to form hydrogen gas. For greatest accuracy, the surface oxides on the contact material should be reduced electrochemically (or chemically) prior to being brought into contact with the part being analyzed. In some instances, where very short lead wires, electrically resistive components, or grid arrays are tested or treated, for example, it may be difficult to make electrical contact without exposing the contact wire to the electrolyte. In this situation, the use of contact material having a high hydrogen overvoltage suppresses parasitic currents associated with hydrogen evolution.

For oxide analysis using the method of the present invention, the applied current is chosen to avoid excessive polarization of the cathode and is typically very small (generally less than about 100 $\mu A/cm^2$) so that the voltage drop in the bulk electrolyte is negligible. The current density is further optimized to provide good resolution and accuracy with an acceptably short analysis time. The electrolyte must be deaerated (via purging with an inert gas) so that electrochemical reduction of oxygen does not interfere with the analysis. Errors associated with reduction of residual oxygen in the electrolyte solution can be mitigated, to some extent, by using a higher current density. The chronopotentiometric measurements of voltage versus charge density obtained from the sequential electrochemical reduction analysis (SERA) indicate the various types and amounts of oxides on the metallic surfaces of the component, as described above. This data is compared with known results from the baseline experiments to characterize the solderability of the component. Although variable voltage and/or current, such as a ramped current, for example, may be used to perform SERA, variation of the independent parameter serves to complicate interpretation of the resulting data.

Figure 3:
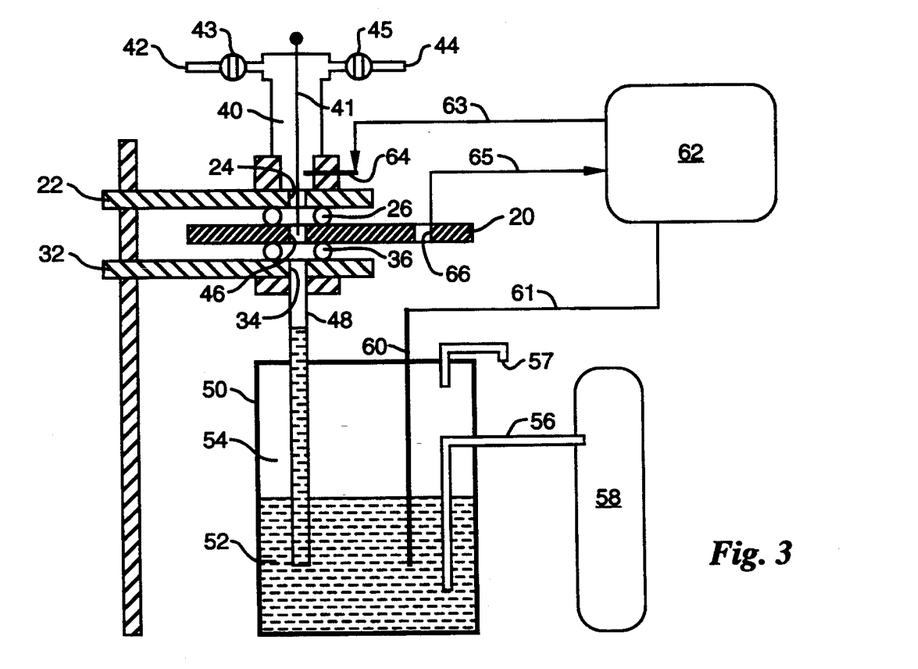
FIG. 3 is a schematic diagram of an apparatus for assessing the solderability of a printed wiring board through-hole electrode.
Figure 4:
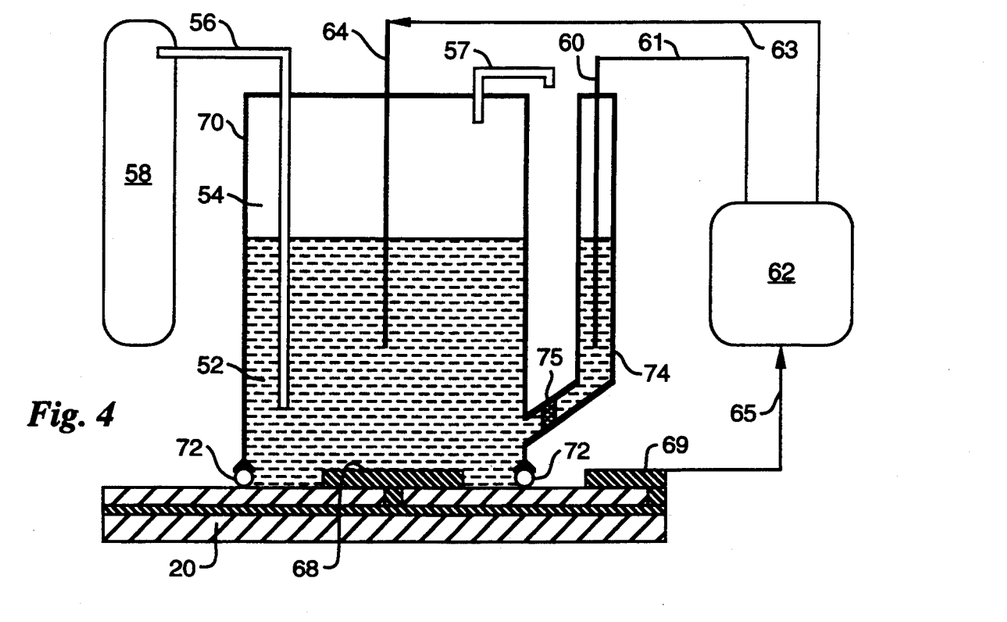
FIG. 4 is a schematic diagram of an apparatus for assessing the solderability of a printed wiring board surface-mount pad electrode.
Figure 5:
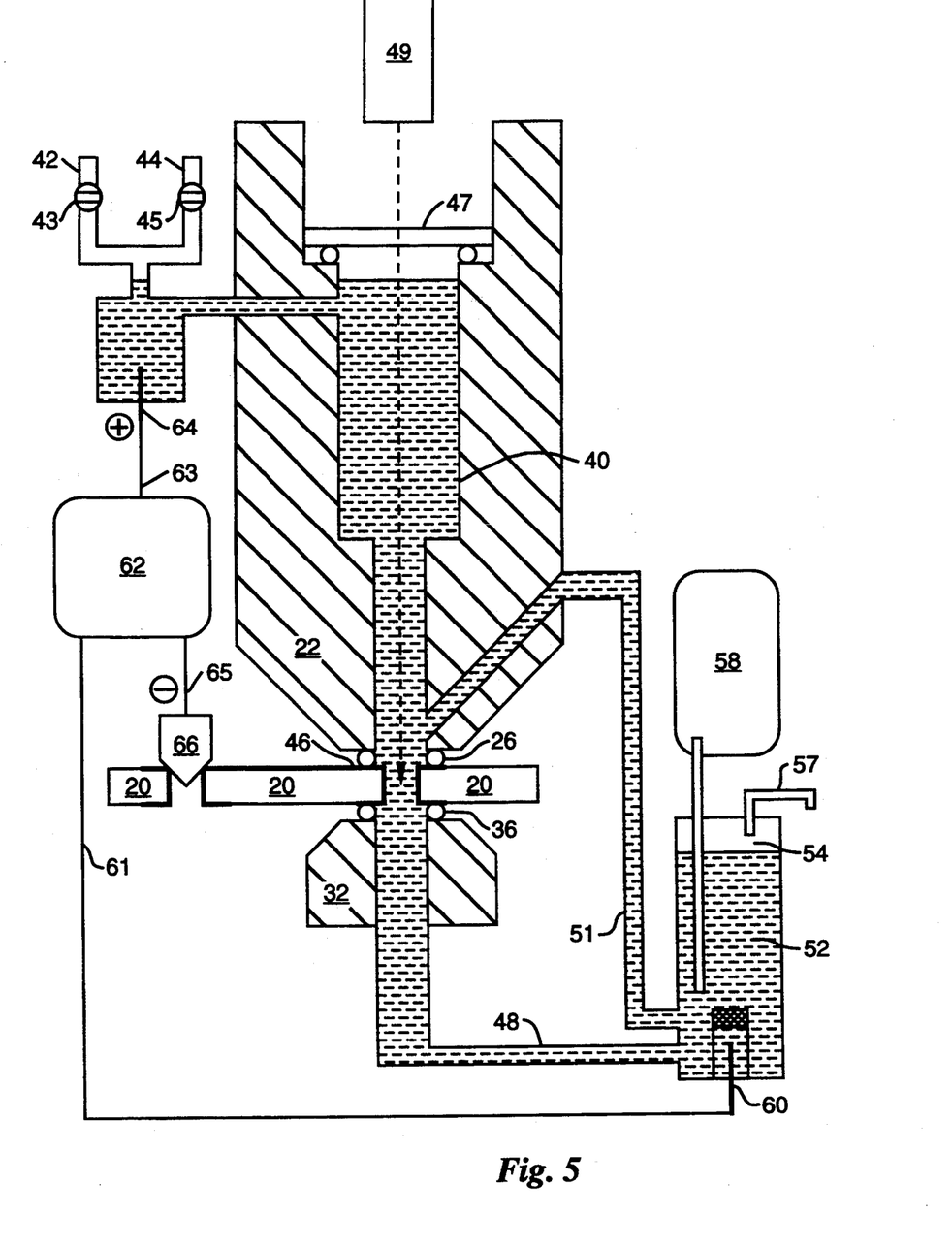
FIG. 5 is a schematic diagram of an apparatus for assessing the solderability of either through-holes or surface-mount pads of printed wiring boards.

Assessing solderability of printed wiring boards can be accomplished with apparatus similar to those depicted schematically in FIGS. 3, 4, and 5. The apparatus of FIG. 3 is primarily for testing circuit board through-hole solderable areas, the apparatus of FIG. 4 is suitable for testing solderable pads (and other flat solderable surfaces) used for surface-mount components, and the apparatus of FIG. 5 is modified for testing either through-holes or pads. The same reference numerals are used in FIGS. 3, 4, and 5 to identify the same or similar components of the several devices. In FIG. 3, a printed wiring board 20 having bare or solder-coated printed copper circuitry to be tested for solderability is clamped between an upper jaw 22 and a lower jaw 32. Upper jaw 22 has an aperture 24 and an O-ring 26. O-ring 26 is attached to the lower side of jaw 22 and encircles aperture 24. Lower jaw 32 has an aperture 34 and an O-ring 36. O-ring 36 is attached to the upper side of jaw 32 and encircles aperture 34. A chamber 40 having a centering pin 41 is mounted atop jaw 22. Chamber 40 is mounted on jaw 22 so that pin 41 can extend downward through aperture 24 in jaw 22. Pin 41 may be used to position a through-hole electrode 46 of printed wiring board 20 between O-rings 26 and 36. Alternative means for positioning circuit boards include the use of light from a source 47, for example, that may be directed through a transparent lid or window 49, as shown in FIG. 5. When circuit board 20 is positioned by pin 41 (or other means) and clamped between jaws 22 and 32, O-rings 26 and 36 provide a seal around through-hole electrode 46 in preparation for assessing solderability of the bare or solder-coated printed copper circuitry associated with through-hole 46.

A tube 48 of inert material extends from aperture 34 of lower jaw 32 into a sealed electrolyte reservoir 50. Reservoir 50 contains an electrolyte solution 52 and an inert gas 54, such as argon, above electrolyte 52. Electrolyte 52 may comprise any electrolyte compatible with the particular solder system, such as a borate buffer solution (9.55 g/L sodium borate and 6.18 g/L boric acid at a pH of 8.4, for example) suitable for use with the Cu—Sn—Pb system. A wide variety of electrolytes (e.g., borates, citrates, sulfates, nitrates, etc.) will provide acceptable results. However, electrolytes having a neutral or alkaline pH, and from which strong metal complexing agents (e.g., chloride, bromide, etc.) have been excluded, will yield the most accurate measurements. Inert gas 54 is supplied to reservoir 50 through a gas line 56 from a gas source 58. Gas 54 can exit reservoir 50 through a gas outlet valve 57. Inert gas 54, such as argon or nitrogen, for example, is used to flush air from the system to eliminate erroneous electrochemical reduction data caused by the presence of oxygen. A reference electrode 60, which may comprise a saturated calomel electrode (SCE), for example, extends into reservoir 50 and into electrolyte 52. Reference electrode 60 may be placed in a separate compartment within reservoir 50 to minimize the effects of any contamination of the electrolyte.

A control system 62, comprising a current (or voltage) source, a voltage (or current) meter, and a recording device, is connected by leads 61, 63, and 65, respectively, to reference electrode 60, an inert counter electrode 64 (such as platinum, for example) that extends within the chamber of chamber 40, and a through-hole contact 66 that is connected by the printed circuitry of circuit board 20 to through-hole electrode 46. In an alternative embodiment, if inert electrode 64 has a stable voltage at the low currents used, it can also function as the reference electrode, thereby eliminating the need for separate reference electrode 60. Furthermore, the need for a separate counter electrode 64 can be eliminated by using centering pin 41 as the counter electrode.

Through-hole electrode 46 is tested for solderability by using pin 41 (or other means) to position through-hole 46 of circuit board 20 between O-rings 26 and 36. Circuit board 20 is clamped securely by jaws 22 and 32 so that O-rings 26 and 36 form a seal around electrode 46. Pin 41 may then be withdrawn from through-hole 46. Chamber 40 is connected to a vacuum line 42 controlled by a valve 43 and to an inert gas line 44 controlled by a valve 45. Valve 45 is opened to flush chamber 40, through-hole 46, and tube 48 with inert gas to remove oxygen from the system. Thereafter, valve 45 is closed and valve 43 is opened so that electrolyte 52 is drawn up through tube 48, through and around electrode 46, and into chamber 40 above counter electrode 64. Alternatively, electrolyte 52 can be pumped from reservoir 50 through tube 48 using a mechanical pump, or it can be forced up through tube 48 by applying gas pressure above electrolyte 52 in reservoir 50.

With electrolyte 52 drawn into chamber 40, system 62 provides a constant current (in the preferred embodiment), in the range of about 10–1000 gA/cm$^2$, through line 63, electrode 64, electrolyte 52, electrode 46, through-hole 66, and line 65 back to source 62 (i.e., a cathodic current is applied to through-hole electrode 46 of circuit board 20). The current provided by source 62 causes sequential electrochemical reduction of the oxides on the bare or solder-coated copper circuitry of through-hole electrode 46. Current greater or less than the recommended 10–1000 $\mu$A/cm$^2$ may be used: if oxygen is purged from the system, a low current provides high resolution at the expense of time; a high current provides faster results but lower resolution. While supplying (and measuring) current, system 62 measures and records the electrode potential between through-hole electrode 46 and reference electrode 60 as a function of time. The time factor can be converted to charge density by multiplying the current density by the elapsed time. As described above, the readout of electrode potential versus charge density (or time) produces a series of inflection points or plateau that indicate the particular oxides being reduced as well as the thicknesses of the various oxide layers. The results can be compared to the baseline data to determine the specific oxides present on electrode 46 and the associated measure of solderability. Although a typical circuit board 20 comprises a multiplicity of through-hole electrodes, a small number of through-holes (a statistical sample) can be tested to characterize the solderability of the entire circuit board 20.

The apparatus shown schematically in FIG. 4 is simply a modification of the foregoing system suitable for testing a solder pad electrode 68 (or other flat solderable surface) on circuit board 20 instead of a through-hole. The modified apparatus comprises an open-bottom vessel 70 that has an O-ring 20 around its bottom rim. Vessel 70 is placed atop board 20 so that O-ring 72 surrounds solder pad electrode 68. Vessel 70 typically includes a lid or port (not shown) for adding electrolyte 52. A clip (not shown) can be used to secure board 20 to the bottom of vessel 70 so that a tight seal is maintained by O-ring 72 around solder pad electrode 68. Inert gas 54 is supplied to vessel 70 by line 56 from gas source 58. After a seal is made around pad electrode 68, vessel 70 may be flushed with inert gas 54, with air escaping from vent 57. Vessel 70 may include a connected chamber 74 with a porous glass frit 75 for partially isolating reference electrode 60. System 62 provides current for electrochemical reduction of the metallic oxides on solder pad electrode 68. Current is provided from control system 62 through line 63, electrode 64, electrolyte 52, pad electrode 68, circuit-connected pad electrode 69, and line 65 back to system 62. System 62 also measures and records the electrode potential between pad electrode 68 and reference electrode 60 as a function of time during electrochemical reduction of the metallic oxides on pad electrode 68. Electrode 60 may be placed in chamber 74, as illustrated, or electrode 64 may function as the reference electrode in some circumstances, thereby eliminating the need for a separate reference electrode 60. As described above, the record of electrode potential versus time can be compared to the baseline data to determine the specific oxides present on pad electrode 68 and the associated measure of solderability.

The devices of FIGS. 3 and 4 can be easily modified, as shown in the apparatus of FIG. 5 for example, to test solder pads as well as through-holes. For testing through-holes, the operation of the apparatus of FIG. 5 is much the same as that described above in conjunction with FIG. 3. For testing solder pads on the top surface of board 20, tube 48 may be closed so that electrolyte 52 is drawn (or forced) up through tube 51 to contact the solder pad and fill chamber 40. Jaws 22 and 32 may be mounted on hinged or retractable arms for ease in aligning the apparatus with the through-holes and/or solder pads to be tested on circuit board 20.

Figure 6:
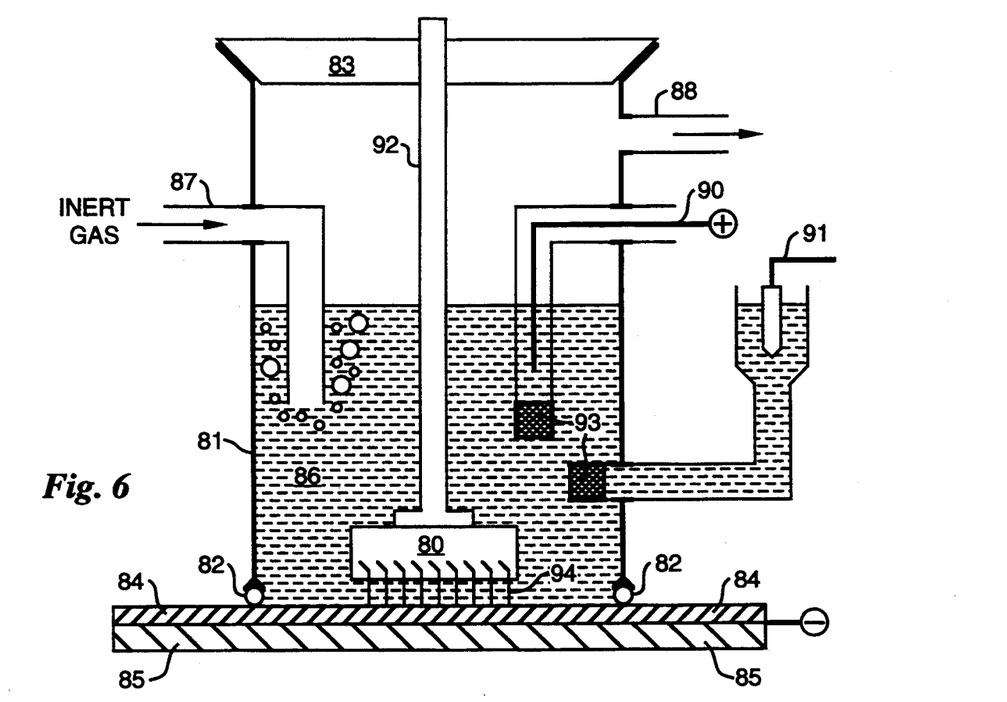
FIG. 6 is a schematic diagram of an apparatus for assessing and restoring the solderability of an electronic component having solderable leads.

The apparatus illustrated schematically in FIG. 6 is suitable for performing sequential electrochemical reduction analysis (SERA) on component leads that are difficult to test without exposing the electrode contact of the testing device to the electrolyte solution. This is the case, for example, when testing short component leads, such as those on dual-in-line package (DIP) component 80 illustrated in FIG. 6, or small solder bumps, pads, or pins distributed in a grid array underneath a component. The apparatus of FIG. 6 is also useful for testing or restoring the solderability of component leads that do not readily permit the passage of direct current, such as capacitors, transistors, and diodes. An electrochemical cell 81 having an O-ring seal 82 at the bottom (for example), is clamped to a cathode 84 having a high hydrogen overvoltage (i.e., a hydrogen overvoltage approximately equal to or greater than that of the metal or alloy being analyzed or restored so as to minimize hydrogen evolution). Thus, cathode 84 may be a foil or plate comprising lead, tin, mercury, indium, antimony, tantalum, bismuth, arsenic, carbon, cadmium, thallium, and alloys thereof, for example, that may be supported by a backing plate 85 of less ductile metal. Cathode 84 may extend over the entire floor of the cell or be patterned to mate with the particular component leads to be tested or restored. The latter arrangement has the advantage of minimizing the area of cathode 84 so as to reduce the magnitude of background currents that might interfere with the analysis. Cell 81 includes a lid 83 that can be removed for adding electrolyte 86 and changing test specimens, such as component 80. To facilitate changing test specimens, all connections to cell 81 can be made through the sides of cell 81. An inlet 87 and an outlet 88 are provided for introducing inert gas into cell 81, as indicated by the direction of the arrows. A counter electrode (anode) 90 and a reference electrode 91 may be placed in electrolyte 86 in separate compartments isolated from the main chamber of cell 81 by glass frits 93, as described above.

Component 80 may be attached (with a quick-drying adhesive, for example) to a rod 92 that can slip through lid 83. Rod 92 may be held in position within cell 81 by a suitable fitting (not shown). Component 80 may be held above electrolyte 86 before testing while any oxides on cathode 84 are reduced electrochemically so that errors are not introduced into the analysis of component 80. Component 80 is then lowered with rod 92 so that electrical lead(s) 94 of component 80 are in contact with both electrolyte 86 and cathode 84. Sequential electrochemical reduction analysis (SERA) is then performed with a control system, such as system 62 described above, to reduce and characterize the oxides on lead(s) 94 of component 80.

The apparatus of FIG. 6 was actually tested to obtain a SERA curve for a DIP component 80. Cathode 84 comprised two Sn metal strips formed by imbedding Sn rods in acrylic potting material and grinding the surface flat. A plating bath masking material was applied to seal the areas where lead(s) 94 exit component 80 to prevent electrolyte 86 from entering component 80. After being electrochemically pre-reduced, the two Sn strips comprising cathode 84 were brought into contact with the two sets of dual in-line lead(s) 94 of component 80, which were then analyzed together at a current density of approximately $-20$ $\mu A/cm^2$.

In a variation of the apparatus of FIG. 6, the component lead(s) 94 to be tested are inserted through hole(s) (not shown) in lid 83 or cell 81 so that the body of component 80 remains outside cell 81. This embodiment avoids the necessity of fully immersing component 80 in solution 86 and permits many components to be tested rapidly in succession because lid 83 does not have to be removed and component 80 does not have to be attached to rod 92. The hole(s) through which lead(s) 94 are inserted for testing may function as vent 88, or may be fitted with a septum that forms a seal around lead(s) 94.

It should be noted that while the apparatus of FIG. 6 is useful for determining the solderability of component lead(s), as in statistical sampling to characterize the solderability of a batch of components, it also restores the solderability of the tested component by actually reducing the metallic oxides that would otherwise have degraded solderability. Therefore, the apparatus and method described above may be used for directly restoring the solderability of component lead(s).

For solderability restoration of electronic parts comprising several components that are not electrically interconnected, as is the case of a completed circuit board, for example, a brush contact (cathode) with many small contact wires (not shown) having a high hydrogen overvoltage can be used. In this embodiment, surface metallic oxides on the electronic part are electrochemically reduced as the cathode wire brush is moved across the part in the electrolyte solution. This arrangement is similar to the method of brush electroplating, except that the use of brush wire material having a high hydrogen overvoltage is essential for attaining negative voltages sufficient to reduce the metallic oxides that degrade solderability.

Although the present invention has been described with respect to specific embodiments thereof, various changes and modifications can be carded out by those skilled in the an without departing from the scope of the invention. Therefore, it is intended that the present invention encompass such changes and modifications as fall within the scope of the appended claims.

We claim:

1. A method of assessing and restoring solderability of an electronic component, comprising the steps of:
   providing an electrolyte in an enclosed vessel having an inert atmosphere;
   placing in said electrolyte a cathode comprising a material having a hydrogen overvoltage at least as high as a solderable portion of the electronic component to minimize evolution of hydrogen from said electrolyte;
   placing said solderable portion of the electronic component in said electrolyte and in contact with said cathode;
   placing a counter electrode in contact with said electrolyte;
   passing an electric current between said cathode and said counter electrode;
   sequentially reducing metallic oxides present on said solderable portion of the component in said electrolyte and in contact with said cathode;
   measuring voltage and current as a function of time during said reduction of metallic oxides; and
   analyzing said voltage and current measurements to assess the solderability of the component.

2. The method of claim 1, wherein the step of measuring said voltage and current comprises measuring said voltage and current between said cathode and said counter electrode as a function of time.

3. The method of claim 1, further comprising the step of providing a third, reference electrode in contact with said electrolyte, and wherein the step of measuring said voltage and current as a function of time comprises measuring said current between said cathode and said counter electrode and said voltage between said cathode and said reference electrode.

4. The method of claim 1, wherein the step of analyzing said voltage and current measurements further comprises:
   comparing said measurements with predetermined baseline data from test specimens having known metallic oxides to identify metallic oxides present on said solderable portion of the electronic component;
   correlating said identified oxides on the electronic component with known solderability of said test specimens.

5. The method of claim 1, further comprising the step of selecting said cathode from the group of materials consisting of lead, tin, mercury, indium, antimony, tantalum, bismuth, arsenic, carbon, cadmium, thallium, and alloys thereof.

6. A method of assessing and restoring solderability of an electronic component by electrochemical reduction of metallic oxides on solderable portions of the component, comprising the steps of:
   providing an electrolyte in a reservoir having an atmosphere of inert gas;
   selecting a cathode from the group of materials consisting of lead, tin, mercury, indium, antimony, tantalum, bismuth, arsenic, carbon, cadmium, thallium, and alloys thereof, and further selecting said cathode to have a hydrogen overvoltage at least as high as the solderable portions of the electronic component to minimize evolution of hydrogen from said electrolyte;
   placing said cathode in said electrolyte;
   providing an inert electrode in contact with said electrolyte;
   placing the solderable portions of the component in contact with said electrolyte and said cathode;
   sequentially reducing the metallic oxides on the solderable portions of the component by passing a current between said cathode and said inert electrode;
   measuring voltage and current as a function of time during said sequential reduction of metallic oxides; and analyzing said voltage and current measurements to assess the solderability of the component.

7. The method of claim 6, wherein the measuring step comprises measuring said voltage and current between said cathode and said inert electrode as a function of time.

8. The method of claim 6, wherein the step of measuring said voltage and current as a function of time further comprises:
placing said inert electrode in a compartment of said reservoir separated with a glass frit;
placing a third, reference electrode in contact with said electrolyte in a second compartment of said reservoir separated with a second glass frit; and
measuring said current between said cathode and said inert electrode and said voltage between said cathode and said reference electrode.

9. The method of claim 6, wherein the step of analyzing said voltage and current measurements further comprises:
comparing said measurements with predetermined baseline data from test specimens having known metallic oxides to identify the metallic oxides on said solderable portions of the component; and
correlating said identified oxides on the component with known solderability of said test specimens.

10. An apparatus for assessing and restoring solderability of an electronic component by electrochemical reduction of metallic oxides on solderable portions of the component, comprising:
a reservoir containing an electrolyte in an atmosphere of inert gas;
a cathode in contact with said electrolyte, said cathode comprising a material selected from the group of materials consisting of lead, tin, mercury, indium, antimony, tantalum, bismuth, arsenic, carbon, cadmium, thallium, and alloys thereof and having a hydrogen overvoltage at least as high as the solderable portions of the electronic component to minimize evolution of hydrogen from said electrolyte;
an inert electrode in contact with said electrolyte;
means placing the solderable portions of the component in contact with said electrolyte and said cathode;
means for sequentially reducing the metallic oxides on the solderable portions of the component by passing a current between said cathode and said inert electrode;
means for measuring voltage and current as a function of time during said sequential reduction of metallic oxides; and
means for analyzing said voltage and current measurements to assess the solderability of the component.

11. The apparatus of claim 10, further comprising a third, reference electrode in contact with said electrolyte.

12. The apparatus of claim 11, further comprising first and second compartments separated from said reservoir by first and second glass frits, respectively, said inert electrode in contact with said electrolyte in said first compartment and said reference electrode in contact with said electrolyte in said second compartment.

13. The apparatus of claim 12, wherein said electrolyte comprises a borate buffer solution and said inert gas comprises argon.

* * * * *